(12) United States Patent
Duncan et al.

(10) Patent No.: US 11,357,477 B2
(45) Date of Patent: Jun. 14, 2022

(54) MICROBUBBLE DESTRUCTION FOR MEDICAL ULTRASOUND IMAGING

(71) Applicant: Siemens Medical Solutions USA, Inc., Malvern, PA (US)

(72) Inventors: David P. Duncan, Renton, WA (US); Gilles D. Guenette, North Bend, WA (US); Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 400 days.

(21) Appl. No.: 16/124,811

(22) Filed: Sep. 7, 2018

(65) Prior Publication Data

US 2020/0077982 A1 Mar. 12, 2020

(51) Int. Cl.
*A61B 8/08* (2006.01)
*A61B 8/06* (2006.01)
*A61K 49/22* (2006.01)
*G01S 7/52* (2006.01)

(52) U.S. Cl.
CPC .............. *A61B 8/481* (2013.01); *A61B 8/06* (2013.01); *A61B 8/483* (2013.01); *A61K 49/223* (2013.01); *G01S 7/52039* (2013.01)

(58) Field of Classification Search
CPC ........... A61B 8/481; A61B 8/06; A61B 8/483; A61B 8/5223; A61B 8/488; A61B 8/5276; A61B 8/5269; A61B 8/4254; A61B 8/44; A61K 49/223; G01S 7/52039
See application file for complete search history.

(56) References Cited

U.S. PATENT DOCUMENTS

| | | | |
|---|---|---|---|
| 4,151,943 A | 5/1979 | Slonaker et al. | |
| 5,456,257 A | 10/1995 | Johnson et al. | |
| 6,240,348 B1 | 5/2001 | Shono et al. | |
| 2003/0092991 A1 | 5/2003 | Sehgal | |
| 2007/0016051 A1 | 1/2007 | Trucco et al. | |
| 2007/0078340 A1* | 4/2007 | Wilcox | G01S 15/8906 600/437 |
| 2008/0125657 A1 | 5/2008 | Chomas et al. | |
| 2011/0230765 A1* | 9/2011 | Guracar | A61B 8/483 600/458 |

(Continued)

FOREIGN PATENT DOCUMENTS

WO 9908599 A1 2/1999
WO WO2004049950 A1 6/2004

(Continued)

OTHER PUBLICATIONS

Extended European Search Report (EESR) dated Nov. 29, 2019 in corresponding European Patent Application No. 19195317.3.

(Continued)

*Primary Examiner* — Bill Thomson
*Assistant Examiner* — Delia M. Appiah Mensah (57) ABSTRACT

By identifying locations of contrast agent response, an intensity-based metric of contrast agent signal is used to control a duration of microbubble destruction with a medical ultrasound scanner. Feedback from motion of the transducer may be used to indicate when a user perceives enough destruction. A combination of both an intensity-based metric and transducer motion may be used to control the duration of bursting.

17 Claims, 2 Drawing Sheets

(56) References Cited

U.S. PATENT DOCUMENTS

2018/0242956 A1* 8/2018 Somerville ........... G06F 1/3203

FOREIGN PATENT DOCUMENTS

| WO | WO-2006013481 A1 * | 2/2006 | ........... A61B 8/0883 |
| WO | 2008039479 A1 | 4/2008 | |
| WO | WO-2008039479 A1 * | 4/2008 | ............. A61B 8/481 |

OTHER PUBLICATIONS

Hansen, C. et al: "A method to expedite data acquisition for multiple spatial-temporal analyses of tissue perfusion by contrast-enhanced ultrasound"; IEEE Transactions on Ultrasonics; Ferroelectrics and Frequency Control; IEEE, US; vol. 56; No. 3; Mar. 1, 2009; pp. 507-519.

Mamou, J., et al. "2D-2 Automatic Detection of Ultrasound Contrast Microbubble Shell Rupture." Ultrasonics Symposium, 2006. IEEE. IEEE, 2006.

* cited by examiner

MICROBUBBLE DESTRUCTION FOR MEDICAL ULTRASOUND IMAGING

BACKGROUND

The present embodiments relate to medical ultrasound imaging of contrast agents (i.e., microbubbles). Destruction of contrast agents and imaging subsequent perfusion, outflow, or inflow of other contrast agents is provided.

Contrast agents may be destroyed by acoustic energy. To image contrast agents, a field of view with little or no contrast agents is desired as a starting point. Sonographers often use bursting or destructive acoustic energy to clear a field of view. For example, the bursting or destruction of the contrast agents may be used to prepare the patient for a second injection or to prepare an acoustic window for imaging contrast agent reperfusion through an organ or tissue of interest.

These burst events are typically user-controlled. For example, the user uses a high-power mode to induce destruction for an arbitrary, finite, or pre-fixed amount of time. By activating the bursting, the high-power acoustic energy is transmitted for a given period. Sufficient contrast agent may not be destroyed in the period, resulting in erroneous measures of perfusion, inflow, or outflow or resulting in the user having to retrigger bursting. The bursting may take longer than needed, resulting is wasted time and undesired destruction of contrast agents in the patient. In some systems, the user activates both the start and ending of the bursting. The variance between users in when to stop may result in inaccurate measurements. User control of both start time and stop time requires excessive user interaction where the user's focus should be on diagnostics. The user may be influenced by tissue response rather than contrast agent signals, so may waste time before stopping the bursting.

SUMMARY

By way of introduction, the preferred embodiments described below include methods, systems, computer readable media, and instructions for microbubble destruction with a medical ultrasound scanner. By identifying locations of contrast agent response, an intensity-based metric of contrast agent signal is used to control a duration of destruction. Feedback from motion of the transducer may be used to indicate when a user perceives enough destruction. A combination of both an intensity-based metric and transducer motion may be used to control the duration of bursting.

In a first aspect, a method is provided for microbubble destruction with a medical ultrasound scanner. A field of view of a patient is imaged with the medical ultrasound scanner. The medical ultrasound scanner identifies locations in the field of view having contrast agents. Acoustic energy generated by the medical ultrasound scanner interleaved with the imaging destroys the contrast agents at the locations. The destruction occurs over a first period. A duration of the first period adapts based on intensity from the contrast agents at the locations and not other locations. The imaging after the first period is continued without continuing the destroying.

In a second aspect, a system is provided for control of contrast agent destruction. A transmit beamformer is configured to cause a transducer to transmit first pulses for destruction of contrast agents and to transmit second pulses for imaging contrast agents with minimal destruction. A receive beamformer is configured to form contrast agent signals responsive to the second pulses. A controller is configured to determine a length of the destruction by the first pulses based on motion of the transducer. An image processor is configured to generate an image responsive to the contrast agent signals after completion of the destruction.

In a third aspect, a method is provided for microbubble destruction with a medical ultrasound scanner. A field of view of a patient is imaged with a transducer of the medical ultrasound scanner. Movement of the transducer during the imaging is detected. Using acoustic energy generated by the medical ultrasound scanner interleaved with the imaging, the contrast agents are destroyed over a first period. A duration of the first period is adapted based on intensity from the contrast agents and on the movement. The imaging continues after the first period without continuing the destroying.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Users may desire to know that perfusion, inflow, or outflow imaging starts from a region cleared of contrast agents. Automated microbubble destruction frees the user to focus on imaging. The automation is more than setting a time. An automatic, data-driven (e.g., image-driven) and/or transducer motion-driven approach controls the amount of microbubble destruction. The ultrasound contrast agent destruction burst mode duration is controlled by (1) an imaging-based bubble destruction index, such as contrast signal intensity or reduced change in contrast signal intensity (i.e., derivative), based on locations of contrast segmented from other anatomy for inclusion or not in the index, and/or (2) probe motion based on a probe motion sensor (e.g., accelerometer) or image-based motion tracking. The intensity-based index and/or reduced motion of the probe during bursting indicates when sufficient contrast agents within an acoustic window are destroyed.

The "destruction index" is a number indicating how much microbubble destruction is occurring within a frame. When the estimated destruction index reaches a particular point (e.g., steady state or passes a threshold), this indicates that the contrast agent within the scanning window is "destroyed." Enough destruction triggers the ultrasound scanner to execute an event, such as stopping the bursting and/or reducing power to avoid bursting.

Where the user desires to destroy contrast agent, the user may move the probe to destroy contrast agents in a three-dimensional region of the patient. With ongoing imaging, the user may see an amount of contrast agent remaining in a region of interest. Once a desired amount of destruction occurs, the user holds the probe in place to view contrast agent re-entry into the region of interest. The ceasing or limiting of the probe movement indicates that destruction is no longer needed, so the bursting is ceased in response to a lack of probe motion.

By using location specific intensity detection and/or probe-based motion detection to cease destruction, the workflow obligations of the user are minimized (e.g., reducing the number of button presses and/or interactions to control bursting). The time used to destroy may be reduced, reducing examination time for the patient and sonographer. The life of remaining contrast agents may be increased, allowing for more effective contrast agent imaging while minimizing the likelihood of further injection and corresponding delays. The contrast agent imaging is made more "plunkable," requiring less training or skill to determine the duration of the bursting.

Figure 1:
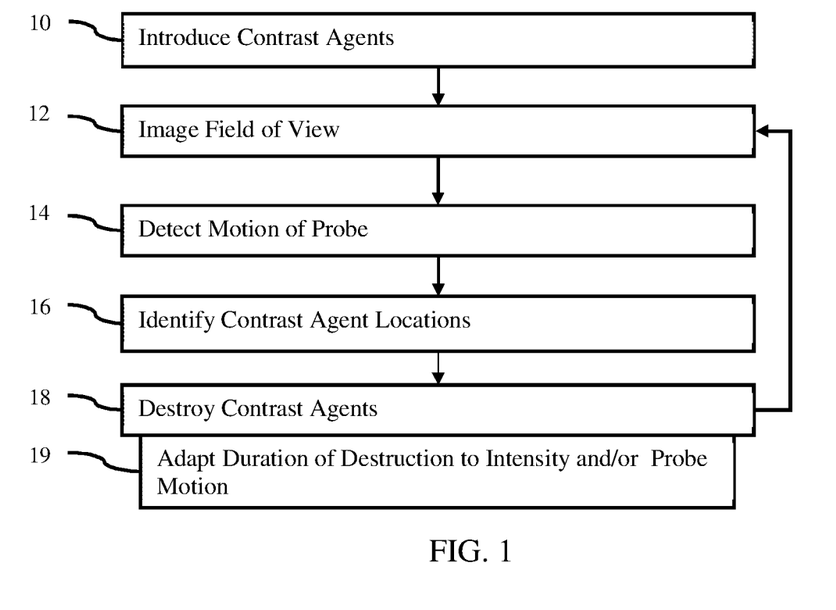
FIG. 1 is a flow chart diagram of a method for microbubble destruction with a medical ultrasound scanner according to one embodiment.

FIG. 1 shows one embodiment of a method for microbubble destruction with a medical ultrasound scanner. The duration of bursting or destruction is controlled based on intensity of contrast agent return from contrast agent specific locations and/or based on an amount of motion of a transducer probe.

Figure 2:
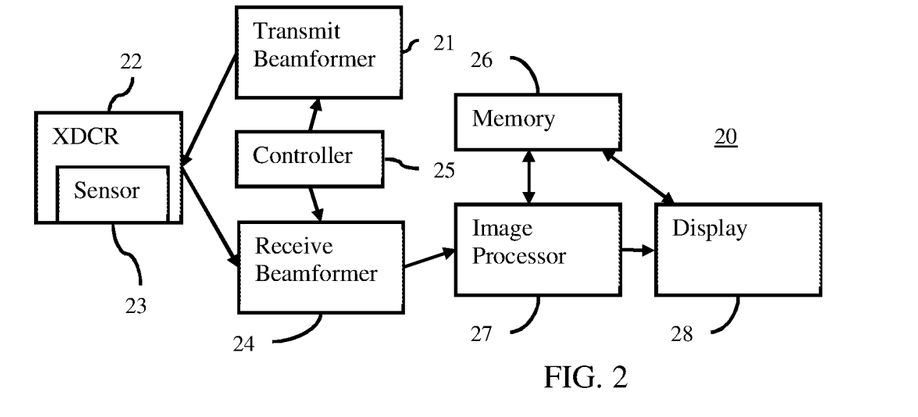
FIG. 2 is a block diagram of one embodiment of an ultrasound imaging system for contrast agent destruction.

The method is implemented by the system 20 of FIG. 2 or a different system. An ultrasound scanner, such as a medical diagnostic ultrasound scanner, images a field of view for contrast agent imaging. Before or during the imaging, a medical professional injects contrast agents into the patient. After imaging any perfusion or flow, contrast agents in the field of view or region of interest may be destroyed to image contrast agent perfusion or flow again. The scanner controls the duration of destruction of contrast agents to allow use of the previously injected contrast agents remaining in the patient or injection of new agents for perfusion or inflow measurements.

The method is performed in the order shown or a different order. For example, act 10 is performed after starting act 12. Act 12 may be performed before destruction of act 18, interleaved with destruction of act 18, and/or continued after ceasing the destruction of act 18. In another example, act 19 is performed as part of act 18. In yet another example, acts 14 and/or 16 are performed in the order shown, a reverse order, or simultaneously.

Additional, different, or fewer acts may be provided. For example, act 14 and/or act 16 are not performed. As another example, an act for displaying a contrast agent image is provided, such as viewing a sequence of images showing perfusion, inflow, and/or outflow of contrast agents. A maximum intensity projection image of maximum contrast agent return by pixel for a period may be generated and displayed.

In act 10, contrast agents are introduced into a patient. The contrast agents are injected as a bolus manually or with a pump through a catheter or syringe. The contrast agents are injected into the bloodstream or other conduction path. The contrast agents may be of any number. In one embodiment, a limited number of contrast agents are injected to reduce the number of free-flowing contrast agents. In another embodiment, a large number of contrast agents are injected.

The contrast agents are microbubbles with or without a shell. the contrast agents are provided for enhanced ultrasound imaging without other therapeutic structure, such as contrast agents for perfusion, inflow, or outflow examination. In other embodiments, the contrast agents may include or be formed from therapeutic material, such as drugs for the treatment of a patient. The surface of the contrast agents may bind to or stick to tissue.

In act 12, a medical ultrasound scanner images a field of view of a patient. A transducer probe is used to transmit and receive acoustic energy for imaging the field of view and/or contrast agents in the field of view. Transmission and reception occur for generating a sequence of ultrasound frames of data representing contrast agents and/or tissue. Acoustic beams with a lower power are transmitted along the scan lines of a region, and echoes responsive to the acoustic beams are received. The lower power is provided by a mechanical index of 0.7 or lower, lower frequency waveforms, smaller aperture, slower pulse repetition frequency, combinations thereof, or another beam characteristic resulting in 33% destruction or less of contrast agents at a focal region.

The region scanned in act 12 includes contrast agents or an area that may include contrast agents. The contrast agents respond to ultrasound energies. Before injection of contrast agents and/or immediately after transmission of destruction pulses, some or the entire region is free of contrast agents. However, one or more locations may have contrast agents due to incomplete destruction and/or rapid in-flow. A given imaging frame of data may include information from contrast agents. The information may also include response from tissue or fluids. Data is acquired at each spatial location of a region of interest in each frame of data.

The imaging is of contrast agents, so includes contrast agent detection. The intensity of contrast agent response to the acoustic energy is determined. Any contrast agent imaging mode may be used. In one embodiment, the response from contrast agents is obtained at a cubic fundamental of ultrasound signals. For example, ultrasound signals are transmitted in a plurality of pulses having at least two different amplitude levels and phases. Received signals responsive to the transmissions are combined. In other embodiments, harmonic imaging is used. By transmitting at one frequency range and detecting response at a harmonic (e.g., second harmonic or twice the transmit frequencies), contrast agents' response may be greater than tissue response. In one embodiment, a B-mode detector and corresponding B-mode detection is used for both contrast agent and tissue information detection. Alternatively, a separate detector, such as Doppler or other detector, is used to detect contrast agent information.

Only one type of data is represented in the frames of data, such as data representing just contrast agents or responses from contrast agent and tissue. Alternatively, the frames of data represent different types of data.

A sequence of frames of data is generated by acquiring frames of data with ultrasound, or by acquiring previously generated ultrasound frames of data (e.g., DICOM images). The frames of data are acquired in real time with live scanning or are from stored clips of detected data. The sequence may be substantially continuous or periodic (e.g., acquired once or more every heart cycle).

The sequence includes frames of data representing a scanned region at different times. Each frame of data represents a same or overlapping region. Some frames may represent different regions, such as due to out-of-plane motion of the transducer relative to the patient.

In act 14, an image processor or controller of the scanner detects motion of the transducer probe. The transducer probe may be moved purposefully or incidentally due to patient or sonographer motion. For destruction, the sonographer may rock, rotate, and/or translate the probe to destroy contrast agents in a three-dimensional or volume region. This may be done for contrast agent imaging in a three-dimensional volume or for reducing immediate inflow for imaging a planar region. The purposeful movement may be distinguished from movement caused by patient breathing or unintentional movement based on the magnitude, duration, direction, or pattern of movement.

The motion of the probe is detected using a sensor or image data. For a sensor, an accelerometer may be used. In other embodiments, a camera or optical sensor, a magnetic positioning sensor, or other motion sensor is used. For image data, motion tracking (e.g., correlation or minimum sum of absolute differences) between frames may indicate an amount and/or direction of movement between frames. By tracking for generally static tissue regions or the entire field of view, organ motion as an error in the detected motion of the transducer may be minimized.

The motion is detected during the imaging of act 12. The motion detection may be limited to after initiation of destruction. Alternatively, the motion of the probe is detected at other times, such as to distinguish a pattern during imaging without destruction from a pattern of movement to destroy.

In act 16, the medical ultrasound scanner (e.g., controller or image processor) identifies one or more (e.g., all) locations in the field of view having contrast agents. The locations are identified in one or more frames of data. For example, the first frame of data after destruction is activated (e.g., the user presses a button to trigger) but before the bursting begins is used. The location of the response from contrast agents is determined from the frame or frames just before destruction begins.

Any segmentation may be used, such as applying a threshold to the contrast agent signals. Any contrast agent intensity above the threshold designates a location of contrast agent. Clustering may be used to limit the locations to one or more connected regions of multiple sample locations above the threshold. Other approaches may be used, such as low pass filtering or machine-learned classifier.

The identification distinguishes between a contrast agent response and an anatomy response (e.g., from a vessel wall). The images or frames of data (B-mode or contrast) of organs or areas of interest are segmented to exclude anatomy that may introduce inaccuracies in the computation of the destruction index based on intensity. The segmentation identifies contrast agent locations by detecting contrast agent and/or by removing tissue locations (i.e., detecting tissue). The segmentation to remove tissue and/or to maintain contrast agent may be conditioned based on the preset chosen by the user or by detected anatomy. For example, the user selects a specific application. The tissue to be detected is identified from the application selection. The appropriate detection for that type of tissue is applied for segmentation.

Responses from tissue, thermal noise, saturation, or other sources that may appear as contrast agent response may be distinguished to further isolate response from contrast agents. A distinction is made between thermal noise, saturation of tissue signals (e.g., non-linear response of tissue signals due to front-end saturation), or both and contrast agent response. Tissue response may cause front-end saturation, leading to false contrast agent signals. Saturation is more likely to occur for reflections from tissue closer to the transducer. The regions in the near field more likely show saturation and tissue signal leakage than other regions. Since the destruction energy is more widely distributed or less focused in the near field, the near field may more likely include undestroyed agent than other regions.

To distinguish, locations associated with tissue are identified. For example, signal from tissue is associated with a large B-mode signal intensity. Using a separate scan or at least some of the beamformed samples from the contrast agent detection, B-mode detection is performed. Locations associated with B-mode data exceeding a threshold are excluded from the contrast agent locations. For contrast agents, locations not associated with tissue are used.

In act 18, the medical ultrasound scanner destroys the contrast agents. The contrast agents at the identified locations and any other locations are destroyed by acoustic energy generated by the scanner.

Before or after any imaging, contrast agents are destroyed. For example, the user views contrast agents and/or tissue during an initial perfusion or inflow of contrast agents. Once the presence of contrast agents and the desired imaging region are confirmed, the contrast agents may be destroyed to calibrate or establish a desired initial condition (e.g., baseline). After destruction, the contrast agents re-perfuse the region of interest. In alternative embodiments, substantial numbers of contrast agents are not destroyed.

Some contrast agents may not be destroyed. The bursting to destroy may be interleaved with the imaging. For example, one or more frames from contrast agent imaging are acquired after transmission of one or more sweeps of a field of view to destroy contrast agents. The imaging and destruction sweeps are repetitively performed in a repeating pattern so that the imaging information may be used to determine a duration of the destruction.

For destruction, acoustic energy sufficient to destroy some or all the contrast agents is transmitted. For example, acoustic energy with a mechanical index 0.7 or higher at one or more locations is transmitted. To assure more likely destruction, a plurality of acoustic beams with a higher power (e.g., MI of 1.0, 1.5, 1.9, or higher) is transmitted along each of a plurality of scan lines. Different or the same focus or other beam characteristics may be used for each beam formed along a scan line. Since acoustic echoes are substantially not received in response to the destruction transmitting, more power may be provided by a short pulse repetition interval. Multiple transmit beams may be used to substantially destroy contrast agents in a given region, such as a scan region or field of view. The region may be a region of interest or an entire field of view.

A plurality of acoustic beams with a relatively higher power than a lower power used in the imaging are transmitted to destroy. Acoustic echoes are substantially not received in response to the transmitting. Substantially is used to account for reverberations from the destruction pulses being received in imaging. For imaging, a plurality of acoustic beams with the relatively lower power than the higher power destructions beams are transmitted. For imaging, echoes from the lower power transmissions are received.

The destruction occurs in response to user triggering or automatically. The user may depress a button to trigger. For example, the user depresses a button to trigger transmission of color Doppler pulses at a high power without reception. A trigger event, such as time or change in intensity, may be used to automatically activate the destruction.

The destruction occurs over a period. During the period, there may be intervals of no transmission while interleaved imaging is performed and corresponding reverberations die down. The intervals are less than a second or 0.5 seconds but may be longer. During the period, imaging and destruction are interleaved at any duty ratio.

The duration of the period during which destruction transmissions occur is dependent on the intensity of imaging return from remaining contrast agents. The instantaneous intensity from a current frame of imaging data and/or change over time (e.g., continuing increase in destruction of the contrast agents) are used to adapt the duration to the specific patient, contrast agent, and tissue of a given examination in act 19. How long the period of destruction lasts may be based, at least in part, on the intensity from the contrast agents during the period. The B-mode or contrast agent mode intensity (e.g., magnitude or power) of return is used to adapt the period.

The intensity is used in an index of contrast agent destruction. This index is created by analysis of image data (e.g., brightness image data, derivative of brightness data, or intensity scalar information). The index is based on intensity from the contrast agents at the locations of contrast agents and not other (e.g., not anatomy or tissue) locations. The intensities from the locations identified in act 16 and not other locations are used in the index. A sub-set of locations of contrast agents may be used, such as contrast agent locations in a region of interest and not including contrast agent locations outside the region of interest. Alternatively, intensities from all or other group of locations are used in the index.

Any index may be used. For example, an average intensity from the contrast agents is calculated from one or more frames of imaging data (e.g., spatial and/or temporal average). Other statistics of the intensity over space and/or time may be used, such as variance or median. As another example, a derivative of intensity is used. The change in intensity or intensity difference over two or more frames of imaging data is calculated. An average change by location or an average change of averages from different frames is used. The scanner adapts the duration of destruction to the change in intensity.

Figure 3:
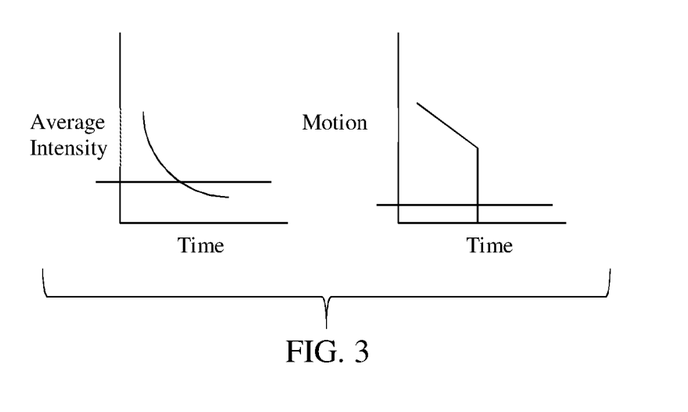
FIG. 3 shows example graphs of an intensity metric and transducer motion as a function of time.

The period ends when the index reaches a threshold level. For example, FIG. 3 shows an average intensity per frame graphed over time. A horizontal line represents a threshold level. With the average intensity of a frame is at or below the threshold, the destruction ceases or is triggered to cease. The period of destruction is adapted to the contrast agents in the specific patient. The period lasts just or only long enough to reach a threshold level of destruction. The comparison of the intensity (e.g., average intensity or amount of change in intensity) to the threshold is repeated during the period of destruction until the threshold is reached, at which point the destruction ceases.

The threshold is fixed or pre-programmed. A user may select a threshold, and/or the threshold may be application specific. The threshold is an absolute number. Alternatively, the threshold is set to be a given amount less than or a percentage of an initially measured index value.

Transducer motion may be used to adapt the duration. The amount of motion, change in motion, and/or pattern of motion is compared to a threshold amount, change, or pattern. FIG. 3 shows an example where the motion is decreasing and then ceases at a given time, resulting in the motion being below a threshold (horizontal line) for a set amount of time. To destroy contrast agents in a volume, the user may move the transducer. The transducer ceasing to move or moving less indicates that the contrast agent destruction is complete. The movement is compared to a threshold. When below the threshold, the period of destruction is ended by the scanner. The threshold is fixed, pre-programmed, user selected, application specific, absolute number, difference from a peak motion, or established in another way.

The intensity index may be used alone to adapt the duration in cases where a single acoustic window (e.g., field of view of the transducer) is being cleared or where the transducer is moved to clear a volume. Alternatively, transducer motion is used to adapt the duration in cases where a volume is to be cleared of contrast agent by a planar field of view. The intensity and transducer motion may be used together to clear a volume. For example, both the index as compared to a threshold and movement as compared to a threshold (e.g., magnitude of movement below a threshold) are to be satisfied to end the period of destruction. As another example, the intensity index and the motion are used in sequence, such as performing the intensity index computation and comparison after the transducer motion is below a threshold and ending the period of destruction upon the intensity being below a threshold. The destroying of act 18 ceases with the intensity below an intensity threshold and the motion below a motion threshold. The duration adapts to both intensity from the contrast agents and on transducer movement.

Once the scanner determines that sufficient contrast agents are destroyed, the period of destruction ceases. The scanner (e.g., transmit beamformer and transducer) stops transmitting the beams for destruction of the contrast agent. In other embodiments, the spatial extent of the destruction decreases, such as continuing to destroy at one region while allowing inflow or perfusion in another region. The transmit beams for destruction in at least one region in the field of view are ceased.

The destruction may be started again, such as after reperfusion or inflow. The ceasing of the destruction is for a given instance until destruction is again triggered. The ceasing of destruction is to allow for continuing or added diagnostic imaging. After the period of destruction ends, the imaging continues (see feedback from act 18 to act 12 of FIG. 1). The continued imaging is the same or different mode or settings. For example, contrast agent mode imaging used for measuring intensity to adapt the period continues for measuring reperfusion and/or inflow. As another example, one or more settings are changed, and/or the imaging mode is changed to image reperfusion and/or inflow as compared to imaging to measure intensity for the index. The imaging continues without continuing the destruction. The imaging uses lower power transmissions to observe reperfusion and/or inflow.

Other events may be triggered and/or performed after or in response to ceasing of the current period of destruction. For example, additional contrast agents are then injected into the patient for further contrast agent imaging. The added contrast agents may be observed in the patient with less contribution from previously injected contrast agents, which have been mostly destroyed.

For the imaging, an image representing perfusion of or inflow to a region of the patient is generated. For example, a baseline frame of data and subsequent frames of data are used to generate a sequence for frames of data showing perfusion. As another example, the frames of data are combined to generate one or more images. One combination is low pass filtering of the frames of data. Another example combination is forming a motion compensated maximum intensity projection image of contrast agent response after the destroying. Frames subsequent to or including a baseline perfusion frame (e.g., first frame after destruction is complete) are accumulated using a motion compensated maximum intensity projection (MIP) over a period, such as accumulating frames of data from 1 to 20 seconds. Any period may be used with the baseline frame acquired at one second or other time. A sequence of images associated with accumulating different periods (e.g., baseline to 5 second, baseline to 10 seconds . . . ) may be generated.

FIG. 2 shows a system 20 for control of contrast agent destruction in medical diagnostic ultrasound imaging. The duration of destruction or bursting is automatically controlled based on intensity from contrast agent locations and/or transducer motion. The system 20 implements the method of FIG. 1 or another method.

The system 20 includes a transmit beamformer 21, a transducer 22, a memory 26, a receive beamformer 24, a controller 25, an image processor 27, and a display 28. Additional, different, or fewer components may be provided. For example, the controller 25 is combined with or part of the image processor 27. As another example, the controller 25 is part of the receive beamformer 24, the transmit beamformer 21, both, or another component.

The system 20 is a medical diagnostic ultrasound imaging system in one embodiment, but other imaging systems of the same (ultrasound) or different modality may be used. In other embodiments, part or all the system 20 is implemented in a computer or workstation. For example, previously acquired frames of data are processed without the beamformers 21, 24 or transducer 22.

The transmit beamformer 21 is an ultrasound transmitter, memory, pulser, analog circuit, digital circuit, or combinations thereof. The transmit beamformer 21 is configured by settings, hardware, firmware, and/or software to generate waveforms for a plurality of channels with different or relative amplitudes, delays, and/or phasing. Upon transmission of acoustic waves from the transducer 22 in response to the generated waveforms, one or more beams are formed. The transmit beamformer 21 may cause the beam to have a particular phase and/or amplitude. For example, the transmit beamformer 21 transmits a sequence of pulses associated with a given scan line or to adjacent scan lines. The pulses correspond to beams with different amplitudes and/or relative phases. In alternative embodiments, a single beam is used for any given scan line and/or beams with a same amplitude and/or relative phases are used.

For contrast agent destruction, waveforms of acoustic energy have a mechanical index of about 1.0 MI or higher. The pulses of acoustic energy cause at least some contrast agents to burst or be absorbed. The frequency, amplitude, power, focus, repetition interval, or other characteristic of the waveforms or acoustic beam may be set to provide the desired destruction. Focal region, beam width, pulse repetition frequency, scan pattern, or other characteristic may be altered to destroy contrast agents more efficiently.

For imaging contrast agents, acoustic energy with a lower mechanical index (MI) is generated. For example, acoustic energy of 0.7 MI or lower is used to limit or avoid destruction of contrast agents. The pulses of acoustic energy cause less contrast agent destruction and are used to measure echo or response to the transmitted acoustic energy. Acoustic energy with higher MI, such as associated with destruction of contrast agents may also be used for imaging.

The transducer 22 is a 1-, 1.25-, 1.5-, 1.75- or 2-dimensional array of elements. The transducer 22 includes a plurality of elements for transducing between acoustic and electrical energies. The elements are piezoelectric or capacitive membrane-based structures. The elements connect with channels of the transmit and receive beamformers 12, 16.

The transducer 22 optionally includes a motion sensor 23. The motion sensor 23 is an accelerometer, magnetic position sensor, or other motion or position sensor for determining motion of the transducer 22. In other embodiments, an optical or other sensor separate from the transducer 22 detects the motion of the transducer 22.

The receive beamformer 24 is configured by firmware, hardware, and/or software to form receive beams sampling the scan region in response to transmitted beams. The receive beamformer 24 includes a plurality of channels with amplifiers, delays, and/or phase rotators, and one or more summers. Each channel connects with one or more transducer elements. The receive beamformer 24 applies relative delays, phases, and/or apodization to form one or more receive beams in response to each imaging transmission. The focused information from the channels is summed dynamically. In alternative embodiments, the receive beamformer 24 is a processor for generating samples using Fourier or other transforms.

The receive beamformer 24 may include a filter, such as a filter for isolating information at a second harmonic or other frequency band relative to the transmit frequency band. Such information may more likely include desired tissue, contrast agent, and/or flow information. In another embodiment, the receive beamformer 24 includes a memory or buffer and a filter or adder. Two or more receive beams are combined to isolate information at a desired frequency band, such as a second harmonic, cubic fundamental, or another band.

The receive beamformer 24 forms contrast agent signals responsive to the ultrasound pulses transmitted for imaging. Signals are not formed (i.e., receive operation not performed) for echoes from transmissions to destroy contrast agents. Alternatively, echoes from destruction transmissions are received for imaging.

Any desired sequence of transmit and receive operation may be used to obtain ultrasound information. For example, B-mode data may be obtained by scanning a region once and detecting the intensity of any response. B-mode may be used for tissue and/or contrast agent imaging. Correlation or motion tracking may be used to derive fluid information from B-mode data. B-mode operation may provide contrast agent information, such as by filtering to isolate information at a second harmonic. Doppler information may be obtained by transmitting sequences of beams along each scan line. A corner turning memory may be used to isolate tissue, contrast agents, and/or flow information from Doppler signals. Other now known or later developed modes may be used.

In one embodiment, the mode is a contrast agent-imaging mode. Contrast agents may be imaged with typical B-mode or Doppler techniques. Contrast agent information is information primarily responsive to contrast agents, and tissue information is information primarily responsive to tissue. Isolating information at the second, even, odd, sub, or other harmonics may more likely identify information from contrast agents. For example, a two-pulse technique is used. The pulses have a same amplitude, but different phase. By summing the response, information associated with even harmonics is identified. Filtering may alternatively be used. Alternatively or additionally, relative phasing is provided in the receive processing.

In one embodiment, the transmit sequence is controlled to generate echo signals responsive to the cubic fundamental. The beamformer 21 is operable to transmit a plurality of pulses having at least two different amplitude levels and at least two of the plurality of pulses having opposite or different phases. Transmitter power may be varied in any suitable manner, as for example by adjusting the voltage applied to individual transducer elements or by adjusting the number of transducer elements (or transmit aperture) used to form a particular pulse.

The controller 25 is a processor, application specific integrated circuit, digital signal processor, field programmable gate array, digital circuit, analog circuit, or combinations thereof. The controller 25 controls operation of the transmit and receive beamformers 12, 16. For example, the controller 25 causes the transmit beamformer 21 to transmit destruction pulses and to cease generation of destruction pulses. As another example, the controller 25 causes the transmit beamformer 21 to transmit imaging pulses and the receive beamformer 24 to receive responsive signals for imaging contrast agents. The controller 25 may control the timing of the transmission of pulses and/or reception.

The controller 25 is configured by firmware, hardware, and/or software to determine a length of time of the destruction by the higher power pulses. The controller 25 is configured to determine the duration or length in time of the destruction pulses based on motion of the transducer 22 and/or intensity from contrast agents at contrast agent locations. The controller 22 uses signals from the sensor 23 and/or information from the image processor 27 to determine motion of the transducer 22. The length of bursting is based on the motion derived from the sensor 23 and/or from imaging data. The controller 25 and/or the imaging processor 27 may determine the motion from imaging data (e.g., image processor 27 calculates a correlation coefficient, which is used by the controller 25 to determine the length). Similarly, the controller 25 and/or the imaging processor 27 may determine locations of contrast agent and/or the intensity index value (e.g., image processor determining locations and index value, which are passed to the controller 25 to determine the length). The image processor 27 may determine the length in other embodiments.

The controller 25 and/or image processor 25 compares the motion of the transducer and/or intensity index value to one or more thresholds to determine the length. When the motion ceases (e.g., below a threshold value over a given time (e.g., 2 seconds)) and/or the intensity (e.g., average intensity or change in average intensity) from the contrast agents during destruction falls below a threshold, the destruction pulses are ended (e.g., the length of destruction is set). The length of time of destruction pulses adapts to the contrast agents remaining during destruction, and the end of the length is determined when the threshold or thresholds are met. A further time for destruction may be included after meeting the threshold or thresholds, such as one second more.

The image processor 27 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting contrast agent and/or tissue information from beamformed ultrasound samples. In one embodiment, the image processor 27 implements a fast Fourier transform from a plurality of samples representing a same region or gate location. Each of the samples is responsive to the cubic fundamental so that pulsed wave Doppler data may be generated from cubic fundamental information. The image processor 27 also includes a B-mode detector in a parallel track. The B-mode detector operates on the same or different beamformed samples to detect tissue, contrast agent, or tissue and contrast agent response. For example, one receive beam for each spatial location from the sequence of receive beams used for cubic fundamental isolation is applied to the B-mode detector for imaging primarily tissue information. Any image processor for detecting contrast agent and/or tissue information may be used, such as a single detector.

The image processor 27 outputs frames of ultrasound data. The frames of data are formatted in an acquisition format (e.g., polar coordinate), a display format (e.g., scan converted into a Cartesian coordinate format or an image), or another format. Each frame of data represents a one, two, or three-dimensional scanned region. The frames of data include a single or multiple types of data. For example, one frame of data includes just contrast agent information. As another example, one frame of data includes contrast agent information for some spatial locations and another type of information (e.g., B-mode or Doppler) for other spatial locations. Different types of data may be provided in the same frame for a same spatial location. In another example, the different types of data are provided in different frames of data.

In an alternative embodiment, the image processor 27 loads data from a network or memory 26. For example, DICOM or other images are loaded. Each image is a frame of data. One frame may include different types of data, one overlaid on another. Alternatively, each frame includes only one type of data with different frames for different data types. In another embodiment, each frame is subdivided so that one portion includes one type of data and another portion includes another type of data with or without overlap of the represented spatial locations.

The image processor 27 may motion track. Different frames through a sequence are correlated to determine an amount of motion and/or direction of motion of the transducer 22. The image processor 27 may detect locations of contrast agent, such as by thresholding, filtering, or applying a machine-learned detector or classifier. The image processor 27 may calculate a value for an intensity index, such as averaging the intensity of contrast agent response from contrast agent locations and not other locations for each frame. Alternatively, the controller 25 performs one or more operations of the image processor 27 using contrast agent information detected by the image processor 27.

The image processor 27 is configured to generate an image. In addition to generating frames of data for controlling destruction, one or more images may be generated. Images of contrast agent and/or tissue may be generated during the destruction period. One or more images may be generated after completion of the destruction. For example, a sequence of B-mode images with contrast agent information used for color modulation shows perfusion after destruction starts. As another example, a maximum intensity temporal projection of contrast agent over time after completion of the destruction is generated. Any contrast agent imaging alone or combined with other modes may be used.

The display 20 is a CRT, monitor, LCD, flat panel, projector or other display device. The display 20 receives display values for displaying an image. The display values are formatted as a one-dimensional image, two-dimensional image, or three-dimensional representation. In one embodiment, the display values are for an image generated as a function of frames of data acquired at different times, such as a time intensity curve (TIC) or maximum intensity projection (MIP) image. As additional frames of data are acquired and selected, the image may be updated. Other images, such as images from single or component frames of data, may also be displayed.

The memory 26 is a buffer, random access memory, read only memory, cache, hard drive, removable, optical, flash, system memory, combinations thereof, or other now known or later developed device for frames of data, images and/or instructions. The memory 26 may be a combination of different memory devices or separately addressed regions. In one embodiment, the memory 26 stores data to be used, during use, or after processing for the processor 27 and/or controller 25.

The image processor 27 and/or controller 25 operate pursuant to instructions. A computer readable storage medium stores data representing instructions executable by one or both of these programmed processors. The instructions for implementing the processes, methods and/or techniques discussed herein are provided on computer-readable storage media or memories 15, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for microbubble destruction with a medical ultrasound scanner, the method comprising:
    imaging a field of view of a patient with the medical ultrasound scanner, the imaging providing data for each location in a region of interest, each location being a sample location;
    identifying, by the medical ultrasound scanner, the locations in the region having contrast agents, the identification of the locations having contrast agents excluding other locations having tissue and no contrast agent, the identification being based on segmenting the locations in the region having the contrast agents from the other sample locations having tissue;
    destroying, with acoustic energy generated by the medical ultrasound scanner interleaved with the imaging, the contrast agents at the locations having contrast agents, the destroying occurring over a first period of time;
    adapting a duration of the first period based on intensity from the contrast agents at the locations that have contrast agents and not the other locations that have tissue as identified based on the segmenting; and
    continuing the imaging after the first period without continuing the destroying.

2. The method of claim 1 wherein destroying comprises transmitting a first plurality of acoustic beams with a higher power than a lower power used in the imaging, wherein acoustic echoes are substantially not received in response to the transmitting.

3. The method of claim 1 wherein identifying comprises distinguishing between a contrast agent response and an anatomy response in the segmenting, the locations having contrast agent response in the region identified with exclusion of the other locations having tissue.

4. The method of claim 1 wherein adapting comprises adapting the duration based on a continuing increase of intensity of the contrast agents during the first time period, the first time period ceasing upon a decrease of the intensity of the contrast agents.

5. The method of claim 1 wherein adapting comprises adapting the duration based on an average intensity from the contrast agents in the imaging.

6. The method of claim 1 wherein adapting comprises adapting the duration so that the destroying ceases due to a change in the intensity from the contrast agents.

7. The method of claim 1 wherein adapting comprises setting the duration based on comparison of the intensity from the contrast agents to a threshold.

8. The method of claim 1 wherein imaging comprises B-mode or contrast agent mode imaging and the intensity from the contrast agents is a B-mode or contrast agent mode measure.

9. The method of claim 1 wherein continuing of the imaging comprises observing reperfusion.

10. The method of claim 1 wherein continuing of the imaging comprises observing the contrast agents from an injection subsequent to the first period.

11. The method of claim 1 wherein imaging comprises imaging with a transducer probe; and
    further comprising detecting motion of the transducer probe; and
    wherein adapting comprises adapting the duration based on the intensity from the contrast agents and the motion.

12. The method of claim 1 wherein identifying comprises identifying the locations having contrast agent while excluding the other locations having tissue and excluding other locations in the region having thermal noise or saturation, and wherein adapting comprises adapting the duration for the locations having contrast agent and not for the other locations having tissue and the other locations having thermal noise or saturation.

13. The method of claim 1 wherein identifying comprises identifying the locations in the region having tissue and not having contrast agents based on B-mode intensity and excluding the locations in the region having tissue and not having contrast agent based on the segmenting of the identifying.

14. The method of claim 1 wherein identifying is performed after triggering the destroying and before destroying occurs.

15. The method of claim 11 wherein adapting the duration comprises ceasing the destroying when the intensity from the contrast agents is below a first threshold and the motion is below a second threshold.

16. A method for microbubble destruction with a medical ultrasound scanner, the method comprising:

imaging a field of view of a patient with a transducer of the medical ultrasound scanner;

detecting movement of the transducer during the imaging;

destroying, with acoustic energy generated by the medical ultrasound scanner interleaved with the imaging, the contrast agents over a first period of time;

adapting a duration of the first period based on intensity from the contrast agents and on the movement where the first period of the destroying ceases when both the movement of the transducer ceases and the intensity is below a threshold; and continuing the imaging after the first period without continuing the destroying.

17. The method of claim 16 further comprising identifying, by the medical ultrasound scanner, locations in the field of view having contrast agents, wherein the intensity from the contrast agents is for the locations and not for other locations in a same region as the locations having contrast agents.

* * * * *